US008697425B2

(12) United States Patent
Yu et al.

(10) Patent No.: US 8,697,425 B2
(45) Date of Patent: Apr. 15, 2014

(54) COMPOSITE YEAST SUITABLE FOR HIGH CONCENTRATION ALCOHOL FERMENTATION

(75) Inventors: Xuefeng Yu, Yichang (CN); Zhihong Li, Yichang (CN); Minghua Yu, Yichang (CN); Juan Yao, Yichang (CN); Zhijun Li, Yichang (CN); Daiwu Liu, Yichang (CN)

(73) Assignee: Angel Yeast Co., Ltd., Yichang, Hubei Province (CN)

( * ) Notice: Subject to any disclaimer, the term of this patent is extended or adjusted under 35 U.S.C. 154(b) by 1336 days.

(21) Appl. No.: 11/914,475

(22) PCT Filed: Dec. 30, 2005

(86) PCT No.: PCT/CN2005/002391
§ 371 (c)(1),
(2), (4) Date: Nov. 15, 2007

(87) PCT Pub. No.: WO2007/009324
PCT Pub. Date: Jan. 25, 2007

(65) Prior Publication Data
US 2008/0187987 A1 Aug. 7, 2008

(30) Foreign Application Priority Data

Jul. 20, 2005 (CN) .......................... 2005 1 0085110

(51) Int. Cl.
*C12N 1/18* (2006.01)
(52) U.S. Cl.
USPC ..................... 435/255.2; 424/93.51; 424/94.2
(58) Field of Classification Search
None
See application file for complete search history.

(56) References Cited

U.S. PATENT DOCUMENTS 6,444,437 B1   9/2002   Sporleder et al.

FOREIGN PATENT DOCUMENTS

| CN | 1201829 | 12/1998 |
|----|---------|---------|
| CN | 1442483 | 9/2003 |
| CN | 1546675 | 11/2004 |
| CN | 1579201 | 2/2005 |
| CN | 1900268 A | 1/2007 |
| JP | 01-132695 | 5/1989 |
| JP | 11-032695 | 2/1999 |
| JP | 11-32695 A | 2/1999 |
| WO | WO 01/60752 A | 8/2001 |
| WO | WO 02/38786 A | 5/2002 |
| WO | WO 2004/013322 | 2/2004 |
| WO | WO 2004/080923 A | 9/2004 |

OTHER PUBLICATIONS

Cenamor et al., Journal of General Microbiology (1987), 133, 619-628.*
Lourens et al. (http://www.wynboer.co.za/recentarticles/0411enzymes.php3), 2000.*
CN 1546675—translation.*
Office Action issued on Aug. 17, 2009 by European Patent Office for corresponding European Application 05824207.4.
Zhang, Qiang et al.: <<Application of Fermentation Intensifier in the Production of Alcohol >>, *Liquor-making Science & Technology*, No. 2, 2004, Tol. 122, pp. 54-57 (in Chinese, with English translation of Abstract, 4 pages).
Zhang, Yan-fang, "Enzymes in winemaking", *SINO-Overseas Grapevine & Wine*, No. 4, 2001, pp. 21-23 (in Chinese, with English translation of Abstract, 3 pages).
Enzyme-Application in Wine Brewing Industry, Novonordisk Company, *SINO-Overseas Grapevine & Wine*, No. 3, 2000, p. 67 (in Chinese, 1 page) with English translation.
Yuan, Hang et al.: <<Applications of enzyme in the manufacturing of beer >>, *Journal of Zhengzhou Institute of Light Industry (Natural Science)*, vol. 15, No. 1, Mar. 2000, pp. 18-23 (in Chinese, 6 pages) with English translation of Abstract.
Search Report issued on Dec. 18, 2008 by European Patent Office for corresponding European Application 05824207.4.
Official action issued by Vietnamese Patent Office, dated Feb. 21, 2012, for corresponding Vietnamese application 1-2007-02249 with English translation.
Official action issued by Canadian Patent Office, dated Apr. 18, 2012, for corresponding Canadian application 2,615,423.
Official action issued by Philippine Patent Office, dated Jun. 21, 2012, for corresponding Philippine application 12008500115.
Zhi-Jun Li et al., Application of Angel Super Dry Yeast in High Gravity Fermentation of Alcohol, Liquor-Making Science & Tech., 2005, pp. 101-106, No. 9, China Academic Journal Electronic Publishing House.
Office Action mailed Nov. 26, 2010 by Canadian Patent Office for counterpart Canadian Application No. 2,615,423.

* cited by examiner

*Primary Examiner* — Irene Marx
(74) *Attorney, Agent, or Firm* — Frommer Lawrence & Haug LLP; Ronald R. Santucci

(57) ABSTRACT

The present invention relates to a composite yeast for high concentration alcohol fermentation, which includes thermostable *Saccharomyces cerevisiae*, acid protease, phytase, cellulose, β-glucanase, and pectinase, and is suitable for the high concentration alcohol fermentation for various raw materials. In addition to normal fermentation, the composite yeast of the present invention can degrade the raw materials, increase the nutrient ingredients in the mash, promote the growth of yeast and provide stress tolerance protection.

3 Claims, No Drawings

COMPOSITE YEAST SUITABLE FOR HIGH CONCENTRATION ALCOHOL FERMENTATION

This application is a 371 of PCT/CN2005/002391 filed on Dec. 30, 2005, published on Jan. 25, 2007 under publication number WO 2007/009324 A which claims priority benefits from Chinese Patent Application No. 200510085110.3 filed Jul. 20, 2005, the disclosure of which is hereby incorporated by reference.

FIELD OF THE INVENTION

The present invention relates to a ferment useful in alcohol fermentation process, and particularly to a composite yeast suitable for high concentration alcoholic fermentation.

BACKGROUND OF THE INVENTION

In the domestic alcoholic fermentation industry, yeast alone or yeast in combination with acid protease is often used to produce alcohol, with the maximum final alcohol content in the mash being 11-12 v/v %. If the final alcohol content in the mash is further increased, the content of residual reducing sugar and starch in the mash would be relatively high, resulting in the decrease of alcohol yield for the raw material and the occurrence of pollution to the environment due to wasted residual reducing sugar, residual starch and alcoholic mash. Therefore, it has become a significant problem in urgent need of settling to increase the final alcohol content in the mash while keeping the contents of residual reducing sugar and residual starch at a relatively reasonable level.

As disclosed in the application "a composite yeast suitable for high concentration alcohol fermentation", filed on Dec. 15, 2003 by the present applicant, a composite yeast comprising thermostable *Saccharomyces cerevisiae*, acid protease, phytase and cellulase is used as a ferment for alcohol fermentation, which may result in the mash of standard raw material such as corn, cassava, and wheat with a final alcohol content of 14.5-15.5 v/v %, with the residual reducing sugar content being controlled at 0.2-0.4 w/v % and the residual starch content being controlled at 1.0-2.0 w/v %.

DISCLOSURE OF THE INVENTION

The objective of the invention is to provide a composite yeast suitable for high concentration alcohol fermentation, which can significantly improve the fermentation efficiency for thermostable *Saccharomyces cerevisiae*, further increase the final alcohol content in the mash, and reduce the content of residual reducing sugar and residual starch based on the prior art, thereby reducing the pressure to the environmental protection.

The objective of the invention is achieved by a composite yeast suitable for high concentration alcoholic fermentation which consists of thermostable *Saccharomyces cerevisiae*, acid protease, phytase, cellulase, β-glucanase, and pectinase. The contents of the ingredients described above are (by weight):
thermostable *Saccharomyces cerevisiae* 61-83%
acid protease 5-30%
phytase 3-10%
cellulase 2-10%
β-glucanase 1-2%
pectinase 1-2%

In a preferred embodiment, the compounding ratios of the ingredients for the composite yeast in the present invention are (by weight):
thermostable *Saccharomyces cerevisiae* 61-78%
acid protease 10-20%
phytase 3-8%
cellulase 5-8%
β-glucanase 1-1.8%
pectinase 1-1.5%

In a more preferred embodiment, the compounding ratios of the ingredients for the composite yeast in the present invention are (by weight):
thermostable *Saccharomyces cerevisiae* 75%
acid protease 12%
phytase 5%
cellulase 5%
β-glucanase 1.5%
pectinase 1.5%

The thermostable *Saccharomyces cerevisiae* in the present invention is a saccharifying strain in the form of solid and particulate, with the content of active cells being generally 35 billion/g. Said *Saccharomyces cerevisiae* converts sugar into alcohol in alcoholic fermentation process. It has the advantages of broad processing temperature range, thermostability, alcohol resistance and high reproductive ability. Also, said yeast is suitable for producing rice wine, liquor, fruit wine, spirits of wine, vinegars, and the like.

Acid protease, phytase, cellulase, β-glucanase, and pectinase act to decompose the raw material and provide nutrients and stress tolerance protection.

Acid protease is an enzyme of grey solid powder with an enzymatic activity being higher than 50,000 u/g; cellulase is an enzyme of grey solid powder with an enzymatic activity being higher than 1,800 u/g; phytase is an enzyme of milk white solid powder with an enzymatic activity being higher than 5,000 u/g; β-glucanase is an enzyme of light yellow solid powder with an enzymatic activity being higher than 800 u/g; and pectinase is an enzyme of light yellow solid powder with an enzymatic activity being higher than 2,000 u/g.

All the raw materials used in the composite yeast of the present invention are commercially available.

As the composite yeast in the present invention is a microbial product, the ingredients are measured by weight. For example, 100 g of the composite yeast product comprises 61-83 g of thermostable *Saccharomyces cerevisiae* (i.e. more than 20 billion per gram), 5-30 g of acid protease (2,500,000-15,000,000 u of enzymatic activity, calculated on the basis of the content of 50,000 u/g, i.e. 2,500-15,000 u/g), 3-10 g of phytase (150,000-500,000 u of enzymatic activity, calculated on the basis of the content of 5,000 u/g, i.e. 150-500 u/g), 2-10 g of cellulase (36,000-180,000 u of enzymatic activity, calculated on the basis of the content of 1,800 u/g, i.e. 36-180 u/g), 1-2 g of β-glucanase (8,000-16,000 u of enzymatic activity, calculated on the basis of the content of 800 u/g, i.e. 8-16 u/g), and 1-2 g of pectinase (20,000-40,000 u of enzymatic activity, calculated on the basis of the content of 2,000 u/g, i.e. 20-40 u/g).

In preparing of the composite yeast of the present invention, the compounding ratios of the ingredients described above may depend on the types of the raw materials used by the alcohol producer. The ingredients are thoroughly mixed together by mechanical or manual agitation, and then packaged into desired specifications.

The composite yeast of the present invention has the advantages of increasing fermented alcohol content, decreasing contents of residual starch and residual reducing sugar, reducing the manufacturing cost of alcohol fermentation, and increasing the yield of wine. It also has the benefits of readily purchasable raw materials, simple manufacture technology, and convenient application. The composite yeast of the present invention can be used as a ferment, for fermentation of standard raw materials such as corn, cassava, and wheat, resulting in a mash liquor with a final alcohol content of 16.0-17.0 v/v %, a residual reducing sugar being controlled at 0.15-0.25 w/v %, and the content of residual starch being controlled at 0.6-1.6 w/v %, thereby decrease the burden to the environmental protection.

EMBODIMENTS OF THE INVENTION

The invention will be further described in detail with reference to examples as follows; however, the scope of protection in the present invention is not limited to these examples.

Examples 1-3

The ingredients of the examples 1-3 are precisely weighed according to the compounding ratios listed in the table 1, agitated for thorough mixing, and packaged as specified to give final products.

Example 4

In this example, corn is used as raw material, and the composite yeast of the present invention is used, for alcohol fermentation. The protocol, amounts of each component being used, and the results are as follows.

The protocol comprises:

1. pulverizing the raw materials: the corn powder is sieved with a mesh of a size of 1.5 mm.

2. moistening the raw materials: adding hot water of 60-70° C. therein according to the final sugar content requirement, and moistening for 30 minutes.

3. liquefaction: adding thermostable amylase in the amount of 10-20 u/g raw materials, liquefying at 95-97° C. for 1.5-2 h, cooling to 32° C., and adjusting with sulfuric acid to a pH of 4.2-4.5.

4. fermentation with the addition of yeast: adding 150-200 u/g of saccharifying enzyme, 0.02% (by weight) of the composite yeast of the present invention, and 0.05% (by weight) of ammonium dihydrogen phosphate, and fermenting at 30-35° C. for 65-68 h.

5. distillation: distilling by a conventional wine fermentation process to obtain alcohol, with the final alcohol content being 16.0-17.0 v/v %, the content of residual reducing sugar being 0.15-0.25 w/v %, and the content of residual starch being 0.6-1.6 w/v %.

Comparative results in alcohol fermentation using the composite yeast of the present invention and using ordinary ferment are shown in table 2:

TABLE 1

| Raw materials (by weight %) | Example 1 | Example 2 | Example 3 | manufacturers | Content of enzymatic activity (content of active cells) |
|---|---|---|---|---|---|
| thermostable *Saccharomyces cerevisiae* | 62 | 75 | 83 | ANGEL YEAST CO., LTD | 35 billion/g |
| acid protease | 20 | 12 | 5 | NOVOZYMES (CHINA) INVESTMENT CO., LTD | 50,000 u/g |
| phytase | 8 | 5 | 5 | NOVOZYMES (CHINA) INVESTMENT CO., LTD | 5,000 u/g |
| cellulase | 8 | 5 | 3 | NOVOZYMES (CHINA) INVESTMENT CO., LTD | 1,800 u/g |
| β-glucanase | 1 | 1.5 | 2 | USTC YIYUAN BIOTECH CO., LTD | 800 u/g |
| pectinase | 1 | 1.5 | 2 | USTC YIYUAN BIOTECH CO., LTD | 2,000 u/g |

TABLE 2

Comparison of final alcohol contents when different ferments are used, residual reducing sugar contents, and residual starch contents

| Composition of ferment (by weight %) | Specific compounding ratio (by weight %) | Final alcohol content in the mash (v/v %) | Content of residual reducing sugar (w/v %) | Content of residual starch (w/v %) |
|---|---|---|---|---|
| Thermostable Saccharomyces cerevisiae 65-85% acid protease 5-30% phytase 3-10% cellulase 2-10% | thermostable Saccharomyces cerevisiae 65% acid protease 20% phytase 10% cellulase 5% | 15.1% | 0.3% | 1.6% |
| | thermostable Saccharomyces cerevisiae 75% acid protease 15% phytase 5% cellulase 5% | 14.6% | 0.39% | 2.0% |
| | thermostable Saccharomyces cerevisiae 85% acid protease 5% phytase 5% cellulase 5% | 15.3% | 0.21% | 1.2% |
| thermostable Saccharomyces Cerevisiae 61%-83% acid protease 5-30% phytase 3-10% cellulase 2-10% β-glucanase 1%-2% pectinase 1%-2% | thermostable Saccharomyces cerevisiae 62% acid protease 20% phytase 8% cellulase 8% β-glucanase 1% pectinase 1% | 16.5% | 0.2% | 1.1% |
| | thermostable Saccharomyces cerevisiae 72% acid protease 15% phytase 5% cellulase 5% β-glucanase 1.5% pectinase 1.5% | 17.0% | 0.17% | 0.6% |
| | thermostable Saccharomyces cerevisiae 83% acid protease 5% phytase 4% cellulase 4% β-glucanase 2% pectinase 2% | 16.1% | 0.24% | 1.5% |

The invention claimed is:

1. A yeast composition suitable for high concentration alcohol fermentation, consisting of thermostable *Saccharomyces cerevisiae*, acid protease, phytase, cellulase, β-glucanase, and pectinase in weight ratios of:
   thermostable *Saccharomyces cerevisiae* 61-83 wt %
   acid protease 5-30 wt %
   phytase 3-10 wt %
   cellulase 2-10 wt %
   β-glucanase 1-2 wt %
   pectinase 1-2 wt %.

2. A yeast composition according to claim 1, wherein the weight ratios are:
   thermostable *Saccharomyces cerevisiae* 61-78 wt %
   acid protease 10-20 wt %
   phytase 3-8 wt %
   cellulase 5-8 wt %
   β-glucanase 1-1.8 wt %
   pectinase 1-1.5 wt %.

3. A yeast composition according to claim 2, wherein the weight ratios are:
   thermostable *Saccharomyces cerevisiae* 75 wt %
   acid protease 12 wt %
   phytase 5 wt %
   cellulase 5 wt %
   β-glucanase 1.5 wt %
   pectinase 1.5 wt %.

* * * * *